US008648199B2

(12) United States Patent
Liu et al.

(10) Patent No.: US 8,648,199 B2
(45) Date of Patent: Feb. 11, 2014

(54) PROCESS FOR MAKING A SOLID-STATE FORM OF AMG 706

(71) Applicant: Amgen Inc., Thousand Oaks, CA (US)

(72) Inventors: Belle Bei Liu, Thousand Oaks, CA (US); Nina Cauchon, Thousand Oaks, CA (US); Gonzalo Alva, Moorpark, CA (US); Pengzu Zhou, Camarillo, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 13/953,602

(22) Filed: Jul. 29, 2013

(65) Prior Publication Data
US 2013/0317227 A1 Nov. 28, 2013

Related U.S. Application Data (60) Continuation of application No. 12/875,844, filed on Sep. 3, 2010, now abandoned, which is a division of application No. 11/636,183, filed on Dec. 7, 2006, now abandoned.

(60) Provisional application No. 60/753,909, filed on Dec. 23, 2005.

(51) Int. Cl.
*C07D 401/14* (2006.01)

(52) U.S. Cl.
USPC .......................................... 546/256

(58) Field of Classification Search
USPC .......................................... 546/256
See application file for complete search history.

(56) References Cited

U.S. PATENT DOCUMENTS

| 5,990,141 | A | 11/1999 | Hirth et al. |
| 6,001,961 | A | 12/1999 | Jonczyk et al. |
| 6,235,764 | B1 | 5/2001 | Larson et al. |
| 6,258,812 | B1 | 7/2001 | Bold et al. |
| 6,284,277 | B1 | 9/2001 | Bouloumie et al. |
| 6,878,714 | B2 * | 4/2005 | Askew et al. .................. 514/256 |
| 6,995,162 | B2 | 2/2006 | Chen et al. |

FOREIGN PATENT DOCUMENTS

| EP | 0386668 A2 | 9/1990 |
| EP | 0 407 122 A1 | 1/1991 |
| EP | 0 770 622 A2 | 5/1997 |
| EP | 0 970 070 B1 | 10/2004 |
| JP | 02233610 A2 | 9/1990 |
| JP | 2279769 A | 11/1990 |
| WO | WO 96/38153 A1 | 12/1996 |
| WO | WO 97/03960 A1 | 2/1997 |
| WO | WO 97/17064 A1 | 5/1997 |
| WO | WO 99/45009 A1 | 9/1999 |
| WO | WO 99/61422 A1 | 12/1999 |
| WO | WO 00/02871 A1 | 1/2000 |
| WO | WO 00/12089 A1 | 3/2000 |
| WO | WO 00/59509 A1 | 10/2000 |
| WO | WO 01/37820 A2 | 11/2000 |
| WO | WO 01/32651 A1 | 5/2001 |
| WO | WO 02/055501 A2 | 7/2002 |
| WO | WO 02/059110 A1 | 8/2002 |
| WO | WO 02/066470 A1 | 8/2002 |
| WO | WO 02/068406 A3 | 9/2002 |
| WO | WO 03/078408 A1 | 9/2003 |
| WO | WO 2004/005279 A3 | 1/2004 |
| WO | WO 2004/007458 A1 | 1/2004 |
| WO | WO 2004/007481 A3 | 1/2004 |
| WO | WO 2004/009784 A3 | 1/2004 |

OTHER PUBLICATIONS

Brittain et al., "Polymorphism in Pharmaceutical Solids", NY: Marcel Dekker, Inc., 1999, pp. 1-2, 183-226.
Bush, et al., "Anti-tumor Activity of Motesanib Diphosphate Alone and in Combination with Docetaxel or Tamoxifen in Xenograft Models of Human Breast Carcinome", Breast Can. Res. And Treatment, 106(1):S77 (2007).
Hawley's "Condensed chemical dictionary" p. 68 (1997).
Lieberman et al., "Pharmaceutical dosage forms" p. 462-465 (1989).
Milano, et al., "New Molecular Targeted Therapies in Thyroid Cancer", Anti-Cancer Drugs, 17(8):869-879 (2006).
Ovid Copyright #037998, "Pharmaprojects", Drug Name, Motesanib Diphosphate, (2007).
Ovid Copyright #11016, "R & D Insight", Drug Name, Motesanib, (2003).
Ovid Copyright #2013210, "R & D Focus", Drug Name, Motesanib, (2004).
Polverino, et al., "AMG 706, an Oral Multikinase Inhibitor that Selectively Targets Vascular Endothelial Growth Factor, Platelet-Derived Growth Factor, and Kit Receptors, Potently Inhibits Angiogenesis and Induces Regression in Tumor Xenografts", Can. Res., 66(77):8715-8721 (2006).
Rosen, et al., "Safety, Pharmacokinetics, and Efficacy of AMG 706, an Oral Multikinase Inhibitor, in Patients with Advanced Solid Tumors", J. of Clin. Oncology, 25(17):2369-2376 (2007).

(Continued)

*Primary Examiner* — Patricia L Morris
(74) *Attorney, Agent, or Firm* — Finnegan, Henderson, Farabow, Garrett & Dunner, LLP (57) ABSTRACT

The anti-angiogenic drug AMG 706 is provided in amorphous form. Also provided is AMG 706 drug substance wherein the AMG 706 is present, in at least a detectable amount, as amorphous AMG 706. Also provided is an AMG 706-crystallization inhibitor composite comprising particles of amorphous AMG 706 or a AMG 706 drug substance of the invention in intimate association with one or more crystallization inhibitors, for example polymers. Also provided is a pharmaceutical composition comprising such an AMG 706-crystallization inhibitor composite and one or more excipients. Also provided are processes for preparing amorphous AMG 706, AMG 706 drug substance of the invention, an AMG 706-crystallization inhibitor composite of the invention, and a pharmaceutical composition of the invention. Also provided is a method of treating a medical condition or disorder in a subject where treatment with an anti-angiogenic is indicated, comprising administering, for example orally, a composition of the invention in a therapeutically effective amount.

3 Claims, 5 Drawing Sheets

(56) References Cited

OTHER PUBLICATIONS

Sherman, et al., "Motesanib Diphosphate in Progressive Differentiated Thyroid Cancer", New England J. of Medicine, 359(1):31-42 (2008).
Sorbera, et al., Oncolytic Antiangiogenic Agent Multikinase Inhibitor, Drugs of the Future, 31(10):847-853 (2006).
SSCI "Amorphous solids . . . " p. 1-3 (2003).
SSCI "Screening for amorphous drug . . . " p. 1-3 (2003).
Wadke, et al., "Pharmaceutical Dosage Forms", 2nd Edition, ed. Herbert A. Lieberman, Published by Marcel Dekker, New York, 1:34-36 (1989).
White et al., "Safety and Pharmacokinetics of Motesanib Diphosphate (AMG 706) with Paclitaxel or Docetaxel for theTreatment of Locally Recurrent, Unresectable or Metastatic Breast Cancer," *Breast Cancer Res Treat*, 30th Annual San Antonio Breast Cancer Symposium—Dec. 13-16, 2007, 106(1):S272 Abstracts—Poster Session VI (2007).

* cited by examiner

XRPD of AMG 706 Amorphous Form from Lyophilization Method

X-ray Tube : Cu(1.54060 A)   Voltage : 40.0 kV   Current : 40.0 mA
Scan Range : 2.5000<-> 40.0000 deg Step Size : 0.0200 deg
Count Time : 12.00 sec Slit DS : 1.00 deg SS 1.00 deg : RS: 0.30 mn FIG.4
DSC of AMG 706, Instrument: Q100

FIG. 5

XRPD of AMG, 706 Instrument: Shimadzu

Condition
X-ray Tube : Cu(1.54060 A)   Voltage : 40.0 kV   Current : 40.0 mA
Scan Range : 2.5000<-> 40.0000 deg Step Size : 0.0200 deg
Count Time :  1.20 sec Slit DS : 1.00 deg SS  : 0.30 mn

PROCESS FOR MAKING A SOLID-STATE FORM OF AMG 706

This is a continuation of application Ser. No. 12/875,844 filed Sep. 3, 2010 (abandoned) which is a divisional of application Ser. No. 11/636,183 filed Dec. 7, 2006 (abandoned) which claims the benefit of U.S. provisional application No. 60/753,909 filed Dec. 23, 2005.

FIELD OF THE INVENTION

The present invention relates to the compound AMG 706, and in particular to solid-state forms of that drug, to pharmaceutical compositions comprising such solid-state forms, and to processes for preparing them. The invention further relates to methods of treatment of angiogenesis mediated disorders comprising administering such solid-state forms or compositions thereof to a subject, and to use of such solid-state forms in the manufacture of medicaments.

DETAILED DESCRIPTION OF THE INVENTION

N-(2,3-Dihydro-3,3-dimethyl-1H-indol-6-yl)-2-[(4-pyridinylmethyl)amino]-3-pyridinecarboxamide, and its pharmaceutically acceptable salts including the diphosphate salt, also known as AMG 706, has a therapeutic and prophylactic anti-angiogenic effect. AMG 706 has utility in treatment and prevention of angiogenesis-mediated disorders, and of such disorders in general.

A need for new forms of AMG 706, in particular forms suitable for preparing rapid-onset compositions, exists. Rapid-onset drug-delivery systems can provide significant benefits over conventional dosage forms. Generally, rapid-onset preparations provide a short period to therapeutic or prophylactic response compared to conventional immediate-release or sustained-release dosage forms.

However, AMG 706 presents certain challenges for formulation as a rapid-onset dosage form, particularly as a rapid-onset oral dosage form. For example, AMG 706 has low solubility in aqueous media and therefore may not have rapid absorption in the gastrointestinal tract when administered orally, for example in tablet or capsule form. In addition, AMG 706 has a moderately high dose requirement further increasing difficulties of providing a sufficient therapeutically effective dose for rapid absorption. For these and other reasons, therefore, it is difficult to prepare an orally deliverable, rapid-onset composition containing AMG 706 that has the desired blend uniformity.

The bioavailability of an orally administered drug, as measured by its entry into systemic circulation in the bloodstream, depends on at least two fundamental processes: drug dissolution in gastrointestinal fluids (in vivo drug release) and subsequent absorption of the dissolved drug. Several factors influence dissolution of a drug from its carrier, including surface area of the drug presented to the dissolution solvent medium, solubility of the drug substance in the solvent medium, and driving forces of the saturation concentration of dissolved materials in the solvent medium.

When the process of in vivo drug release is slower than the process of absorption, absorption is said to be dissolution rate-limited. Since dissolution precedes absorption in the overall process, any change in the drug release or dissolution process will subsequently influence drug absorption. See for example, Lieberman et al., Pharmaceutical Dosage Forms: Tablets, Marcel Dekker, New York, 1, 34-36 (1989). It is clear, therefore, that dissolution time determined for a composition is one of the important fundamental characteristics for consideration when evaluating compositions intended for fast-onset delivery, particularly where drug absorption is dissolution rate-limited.

Crystalline solids, due to their highly organized, lattice-like structures, typically require a significant amount of energy for dissolution. The energy required for a drug molecule to escape from a crystal, for example, is greater than is required for the same drug molecule to escape from a non-crystalline, amorphous form. Importantly, however, crystalline drug forms which have been transformed into amorphous forms tend to revert to a steady state of low energy, namely the crystalline form, over time and thus may not have an adequate shelf life. An amorphous form of AMG 706 has not hitherto been known in the art.

As indicated hereinbelow, treatment with AMG 706 is indicated in a very wide array of angiogenesis-mediated conditions and disorders. Therefore, if an amorphous form of AMG 706 could be prepared, and in particular if a storage-stable composition comprising such an amorphous form of AMG 706 could be developed exhibiting enhanced bioavailability, for example through rapid dissolution of the drug, a significant advance would be realized in treatment of angiogenesis mediated conditions and disorders.

AMG 706 provides better solubility or a more rapid onset of therapeutic effect if, upon oral administration of a composition comprising AMG 706, pharmacokinetic properties are exhibited leading to a greater maximum blood serum concentration ($C_{max}$) and/or a shorter time following the administration to reach that maximum ($T_{max}$). It is contemplated that a greater $C_{max}$ and/or a shorter $T_{max}$ can result from faster dissolution of AMG 706 when provided in amorphous form than in crystalline form.

Accordingly, the present invention provides amorphous AMG 706. There is also provided AMG 706 drug substance wherein the AMG 706 is present, in at least a detectable amount, as amorphous AMG 706. The term "AMG 706 drug substance" as used herein means AMG 706 per se as qualified by the context in which the term is used, and can refer to unformulated AMG 706 or to AMG 706 present as an ingredient of a pharmaceutical composition.

Alternatively, there is provided an AMG 706-crystallization inhibitor composite comprising particles of amorphous AMG 706 or AMG 706 drug substance of the invention in intimate association with one or more crystallization inhibitors. The crystallization inhibitors are selected and present in an amount sufficient to substantially reduce conversion of amorphous AMG 706 to crystalline AMG 706. Preferred crystallization inhibitors are polymers that form with the AMG 706 an AMG 706-polymer composite.

Also provided are processes for preparing amorphous AMG 706, and for preparing AMG 706 drug substance of the invention.

AMG 706 drug substance or powder thereof, prepared according to such processes can be further formulated to provide a pharmaceutical dosage form.

Also provided is a method of treating a medical condition or disorder in a subject where treatment with an angiogenesis inhibitor is indicated, comprising administering, for example orally, a composition of the invention in a therapeutically effective amount. Such method is particularly useful where the medical condition or disorder is angiogenesis.

Other features of this invention will be in part apparent and in part pointed out hereinafter.

AMORPHOUS AMG 706

The invention provides a novel amorphous form of AMG 706. The term "amorphous", as used herein, refers to solid-state particles lacking a regular crystalline structure. Without being bound by theory, it is believed that amorphous AMG 706 particles require less energy for dissolution than crystalline AMG 706 particles of similar dimensions, and that this reduced dissolution energy requirement contributes, at least in part, to increased dissolution rate and/or decreased therapeutic onset time exhibited by amorphous AMG 706 and compositions thereof.

In addition to amorphous AMG 706 per se, the invention provides AMG 706 drug substance that comprises amorphous AMG 706. At least a detectable amount of amorphous AMG 706 is present. Preferably, about 10% to about 100%, more preferably about 25% to about 100%, still more preferably about 60% to about 100%, and even more preferably about 80% to about 100%, by weight of the AMG 706 in an AMG 706 drug substance of the invention is amorphous. In a particular embodiment, substantially all of the AMG 706 is amorphous, i.e., the AMG 706 drug substance is substantially phase pure amorphous AMG 706.

In one embodiment, the amount of amorphous AMG 706 in an AMG 706 drug substance is sufficient to provide increased dissolution rate as measured in a standard in vitro dissolution assay and/or improved bioavailability (e.g., shorter time to reach a threshold therapeutic concentration in blood plasma, greater $C_{max}$ and/or shorter $T_{max}$) as measured in a standard in vivo pharmacokinetic study, compared with an otherwise similar AMG 706 drug substance wherein all, or a substantial portion of, the AMG 706 is crystalline.

Amorphous AMG 706 or AMG 706 drug substance of the invention can be prepared by any suitable process, not limited to processes described herein. One illustrative process comprises a step of spray-drying a solution of AMG 706. One illustrative process comprises a lyophilization step on a solution of AMG 706. One process for preparing AMG 706 drug substance of the invention comprises (a) a step of dissolving AMG 706 in a suitable solvent such as water; and (b) a step of spray-drying the resulting solution. Another process includes the cryogenic milling of AMG 706.

AMG 706 drug substance or drug powder prepared according to the above process or any other process can be administered orally, rectally or parenterally without further formulation, or in simple suspension in water or another pharmaceutically acceptable liquid. Alternatively, the AMG 706 drug substance or drug powder can be directly filled into capsules for oral administration. Preferably, however, AMG 706 drug substance or drug powder is subjected to further processing, typically with one or more excipients, to prepare a pharmaceutical composition, for example an oral dosage form, as described hereinbelow.

AMG 706-Crystallization Inhibitor Composites

In a presently preferred embodiment of the invention there is provided an AMG 706-crystallization inhibitor composite comprising particles of amorphous AMG 706 or a AMG 706 drug substance having at least a detectable amount of amorphous AMG 706, in intimate association with one or more crystallization inhibitors. An "intimate association" in the present context includes, for example, AMG 706 admixed with the crystallization inhibitor, AMG 706 embedded or incorporated in the crystallization inhibitor, AMG 706 forming a coating on particles of the crystallization inhibitor or vice versa, and a substantially homogeneous dispersion of AMG 706 throughout the crystallization inhibitor. The term "substantially homogeneous" herein with reference to a composite or pharmaceutical composition that comprises multiple components means that the components are sufficiently mixed such that individual components are not present as discrete layers and do not form concentration gradients within the composition.

An AMG 706-crystallization inhibitor composite of this embodiment preferably comprises about 1% to about 95%, preferably about 10% to about 90%, more preferably about 25% to about 85%, and still more preferably about 30% to about 80%, by weight, of AMG 706. As indicated above, AMG 706 in such a composite exists, at least in a detectable amount, in amorphous form. Preferably, about 10% to about 100%, more preferably about 25% to about 100%, still more preferably about 60% to about 100%, and even more preferably about 80% to about 100%, by weight of the total AMG 706 in the composite is amorphous AMG 706. In composites of this embodiment, a fraction of the AMG 706 can be present as microcrystalline or nanocrystalline AMG 706, though this fraction is preferably small, for example less than about 50%, more preferably less than about 25%, and still more preferably less than about 10%, by weight of the total AMG 706 in the composite.

Crystallization inhibitors include any material which substantially reduces conversion of amorphous AMG 706 to crystalline AMG 706, for example, polymers, carbohydrates, lipids, etc. The term "substantially" with respect to reducing such conversion includes completely inhibiting, preventing, slowing, delaying, decreasing or restricting crystallization of AMG 706 to a measurable degree. It will be understood that both selection of crystallization inhibitor(s) and the amount of crystallization inhibitor(s) used in a composite of the invention influences stability of amorphous AMG 706 therein. Crystallization inhibitors are preferably polymers, more preferably polymers of low solubility in water. Still more preferably, such polymers are substantially non-crosslinked.

Non-limiting examples of suitable polymers that can be used as crystallization inhibitors include, either alone or in combination, polyvinylpyrrolidone (PVP or povidone, e.g., Kollidon™ CLM of BASF), hydroxypropylmethylcellulose (HPMC, e.g., Methocel™ E5 Premium), HPMC phthalate, ethylcellulose, hydroxyethylcellulose, sodium carboxymethylcellulose (carmellose sodium), calcium carboxymethylcellulose, dextran, acacia, starches such as sodium starch glycolate (SSG, e.g., Explotab™), β-cyclodextrin (e.g., Kleptose™ 4PC of Roquette), block copolymers of ethylene oxide and propylene oxide (e.g., Pluronic™ F-68 and F-108), polyvinyl alcohol and polyethylene glycol (PEG). Povidone and HPMC are preferred polymers for use as crystallization inhibitors and form AMG 706-polymer composites of the invention.

HPMCs vary in the chain length of their cellulosic backbone and consequently in their viscosity as measured for example at a 2% by weight concentration in water. HPMC used in AMG 706-polymer composites of the invention should have a viscosity, 2% in water, of about 100 to about 100,000 cP, preferably about 1000 to about 15,000 cP, for example about 4000 cP. Molecular weight of HPMC used in AMG 706-polymer composites of the invention is preferably greater than about 10,000 but preferably not greater than about 1,500,000, more preferably not greater than about 1,000,000, still more preferably not greater than about 500,000, and even more preferably not greater than about 150,000.

HPMCs also vary in the relative degree of substitution of available hydroxyl groups on the cellulosic backbone by methoxy and hydroxypropoxy groups. With increasing hydroxypropoxy substitution, the resulting HPMC becomes more hydrophilic in nature. It is preferred in AMG 706-HPMC composites of the present invention to use HPMC having about 15% to about 35%, preferably about 19% to about 32%, and more preferably about 22% to about 30%, methoxy substitution, and having about 3% to about 15%, preferably about 4% to about 12%, and more preferably about 7% to about 12%, hydroxypropoxy substitution.

HPMCs which can be used in the present invention are illustratively available under the brand names Methocel™ of Dow Chemical Co. and Metolose™ of Shin-Etsu Chemical Co. Examples of particularly suitable HPMCs having medium viscosity include Methocel™ E4M and Methocel™ K4M, both of which have a viscosity, 2% in water, of about 4000 cP. Examples of HPMCs having higher viscosity include Methocel™ E10M, Methocel™ K15M and Methocel™ K100M, which have viscosities, 2% in water, of 10,000 cP, 15,000 cP and 100,000 cP respectively. Preferred povidones used in AMG 706-polymer composites of the invention have a molecular weight of about 2,500 to about 3,000,000, preferably about 8,000 to about 1,000,000, and more preferably about 10,000 to about 400,000, for example, about 50,000. Preferably, povidone used in AMG 706-polymer composites have a dynamic viscosity, 10% in water at 20° C., of about 1.3 to about 700, preferably about 1.5 to about 300, and more preferably about 3.5 to about 8.5 mPas.

In AMG 706-crystallization inhibitor composites, for example AMG 706-polymer composites, of the invention, the amount of crystallization inhibitor is preferably sufficient such when maintained in an open dish at ambient temperature for a period of 7 days, transformation of amorphous AMG 706 to crystalline AMG 706 is no greater than about 50%, preferably no greater than about 25%, and more preferably no greater than about 10%, by weight of all AMG 706 in the composite. Typically, depending on the particular polymer(s) used, one or more polymers are present in a contemplated AMG 706-polymer composite in a total amount of about 10% to about 80%, preferably about 15% to about 75%, and more preferably about 25% to about 65%, by weight. Preferably, the weight ratio of AMG 706 to polymer is about 1:1000 to about 10:1, more preferably about 1:10 to about 5:1, and still more preferably about 1:2 to about 2.5:1.

An AMG 706-crystallization inhibitor composite of the invention can be prepared by any suitable process, not limited to processes described herein. One illustrative process comprises (a) a step of dissolving AMG 706 and one or more crystallization inhibitors in a solvent liquid to form a solution; and (b) a step of drying the solution to form a AMG 706-crystallization inhibitor composite wherein the AMG 706 and the crystallization inhibitor are in intimate association and wherein at least a detectable fraction of the AMG 706 is in amorphous form. Optionally, this process can further comprise a step (c) of grinding the AMG 706-crystallization inhibitor composite to form an AMG 706-crystallization inhibitor composite powder. Suitable solvent liquids which can be used to prepare an AMG 706-crystallization inhibitor composite, for example an AMG 706-polymer composite, can comprise any pharmaceutically acceptable solvent in which AMG 706 can be dissolved. Heat and stirring can be used to facilitate drug dissolution in the solvent liquid. The solvent liquid can also comprise a non-solvent fraction, for example, water. Non-limiting examples of suitable solvents that may be used in solvent liquids of the invention include, for example, water-alcohol mixtures, methanol, ethanol, isopropanol, higher alcohols, propylene glycol, ethyl caprylate, propylene glycol laurate, polyethylene glycol (PEG), diethyl glycol monoethyl ether (DGME), tetraethylene glycol dimethyl ether, triethylene glycol monoethyl ether, polysorbate 80, etc. Water, ethanol, and isopropanol are preferred solvents.

The drying step (b) can be performed by any suitable means, for example, by evaporation, lyophilization, conventional heating (e.g., in an oven), spray drying, etc. Spray drying is a preferred method of drying. Any suitable spray drying method known in the art can be employed. Generally, spray drying is a process by which a solution comprising dissolved drug and crystallization inhibitor is rapidly sprayed over a current of warm air, resulting in formation of dry powder.

The optional grinding step (c) can be performed by any suitable method, for example by grinding in a mortar and pestle or by grinding in a mill, for example a media mill.

An AMG 706-crystallization inhibitor composite, for example AMG 706-polymer composite or a powder thereof, prepared according to the above process or any other processes can be administered orally, rectally or parenterally without further formulation, or in simple suspension in water or another pharmaceutically acceptable liquid. Alternatively, the composite or powder thereof can be directly filled into capsules for oral administration. Preferably, however, the composite or powder thereof is subjected to further processing, typically with one or more additional excipients, to prepare a pharmaceutical composition, for example an oral dosage form, as described hereinbelow.

Pharmaceutical Compositions

"Pharmaceutically acceptable" means that which is useful in preparing a pharmaceutical composition that is generally non-toxic and is not biologically undesirable and includes that which is acceptable for veterinary use and/or human pharmaceutical use.

The term "composition" includes but is not limited to a solution, a suspension, a gel, an ointment, an emulsion and/or mixtures thereof. The term composition is intended to encompass a product comprising the specified ingredients in the specified amounts, as well as any product, which results, directly or indirectly, from combination of the specified ingredients in the specified amounts. A "composition" may contain a single compound or a mixture of compounds.

The term "pharmaceutical composition" is intended to encompass a product comprising the active ingredient(s), pharmaceutically acceptable excipients that make up the carrier, as well as any product which results, directly or indirectly, from combination, complexation or aggregation of any two or more of the ingredients, or from dissociation of one or more of the ingredients, or from other types of reactions or interactions of one or more of the ingredients. Accordingly, the pharmaceutical compositions of the present invention encompass any composition made by admixing one of the dihydrochloride salts of cetirizine described by the present invention, additional active ingredient(s), and pharmaceutically acceptable excipients.

"Therapeutically effective amount" means the amount of a compound that, when administered for treating or preventing a disease, is sufficient to effect such treatment or prevent the disease. The "therapeutically effective amount" will vary depending on the compound, the disease and its severity and the age, weight, etc., of the patient to be treated.

Amorphous AMG 706, AMG 706 drug substance or AMG 706-crystallization inhibitor composite as provided herein can be further formulated together with one or more pharmaceutically acceptable excipients to produce a pharmaceutical composition. The term "excipient" herein means any substance, not itself a therapeutic agent, used as a carrier or vehicle for delivery of a therapeutic agent to a subject or added to a pharmaceutical composition to improve its handling or storage properties or to permit or facilitate formation of a dose unit of the composition into a discrete article such as a capsule or tablet suitable for oral administration. Excipients include, by way of illustration and not limitation, diluents, disintegrants, binding agents, adhesives, wetting agents, lubricants, glidants, crystallization inhibitors, surface-modifying agents, substances added to mask or counteract a disagreeable taste or odor, flavors, dyes, fragrances, and substances added to improve appearance of the composition.

Excipients employed in compositions of the invention can be solids, semi-solids, liquids or combinations thereof. Compositions of the invention containing excipients can be prepared by any known technique of pharmacy that comprises admixing an excipient with a drug or therapeutic agent. A composition of the invention contains a desired amount of AMG 706 per dose unit and, if intended for oral administration, can be in the form, for example, of a tablet, a caplet, a pill, a hard or soft capsule, a lozenge, a cachet, a dispensable powder, granules, a suspension, an elixir, a liquid, or any other form reasonably adapted for such administration. If intended for parenteral administration, it can be in the form, for example, of a suspension. If intended for rectal administration, it can be in the form, for example, of a suppository. Presently preferred are oral dosage forms that are discrete dose units each containing a predetermined amount of the drug, such as tablets or capsules.

Non-limiting examples follow of excipients that can be used to prepare pharmaceutical compositions of the invention. Compositions of the invention optionally comprise one or more pharmaceutically acceptable diluents as excipients. Suitable diluents illustratively include, either individually or in combination, lactose, including anhydrous lactose and lactose monohydrate; starches, including pregelatinized starch; mannitol; sorbitol; xylitol; dextrose and dextrose monohydrate; dibasic calcium phosphate dihydrate; sucrose-based diluents; confectioner's sugar; monobasic calcium sulfate monohydrate; calcium sulfate dihydrate; dextrates; inositol; amylose; celluloses including microcrystalline cellulose and powdered cellulose; calcium carbonate; glycine; bentonite; polyvinylpyrrolidone; and the like. Such diluents, if present, constitute in total about 5% to about 99%, preferably about 10% to about 85%, and more preferably about 20% to about 80%, of the total weight of the composition. The diluent or diluents selected preferably exhibit suitable flow properties and, where tablets are desired, compressibility. Pregelatinized starch and microcrystalline cellulose, either individually or in combination, are preferred diluents. Both diluents are chemically compatible with AMG 706. The use of extra-granular microcrystalline cellulose (that is, microcrystalline cellulose added to a wet granulated composition after a drying step) can be used to improve hardness (for tablets) and/or disintegration time.

Compositions of the invention optionally comprise one or more pharmaceutically acceptable disintegrants as excipients, particularly for tablet formulations. Suitable disintegrants include, either individually or in combination, starches, including sodium starch glycolate (e.g., Explotab™ of PenWest) and pregelatinized corn starches (e.g., National™ 1551, National™ 1550, and Colocorn™ 1500), celluloses such as purified cellulose, microcrystalline cellulose, methylcellulose, carboxymethylcellulose and sodium carboxymethylcellulose, croscarmellose sodium (e.g., Ac-Di-Sol™ of FMC), alginates, crospovidone, and gums such as agar, guar, locust bean, karaya, pectin and tragacanth gums. Disintegrants may be added at any suitable step during the preparation of the composition, particularly prior to granulation or during a lubrication step prior to compression. Such disintegrants, if present, constitute in total about 0.2% to about 30%, preferably about 0.2% to about 10%, and more preferably about 0.2% to about 5%, of the total weight of the composition. Croscarmellose sodium and crospovidone are preferred disintegrants for tablet or capsule disintegration, and, if present, preferably constitutes about 0.2% to about 10%, more preferably about 0.2% to about 7%, and still more preferably about 0.2% to about 5%, of the total weight of the composition. Both croscarmellose sodium and crospovidone confers superior intragranular disintegration capabilities to granulated compositions of the present invention.

Compositions of the invention optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, either individually or in combination, acacia; tragacanth; sucrose; gelatin; glucose; starches such as, but not limited to, pregelatinized starches (e.g., National™ 1511 and National™ 1500); celluloses such as, but not limited to, methylcellulose and carmellose sodium (e.g., Tylose™); alginic acid and salts of alginic acid; magnesium aluminum silicate; PEG; guar gum; polysaccharide acids; bentonites; povidone, for example povidone K-15, K-30 and K-29/32; polymethacrylates; HPMC; hydroxypropylcellulose (e.g., Klucel™); and ethylcellulose (e.g., Ethocel™). Such binding agents and/or adhesives, if present, constitute in total about 0.5% to about 25%, preferably about 0.75% to about 15%, and more preferably about 1% to about 10%, of the total weight of the composition.

Compositions of the invention optionally comprise one or more pharmaceutically acceptable wetting agents as excipients. Such wetting agents are preferably selected to maintain the AMG 706 in close association with water, a condition that is believed to improve bioavailability of the composition. Non-limiting examples of surfactants that can be used as wetting agents in compositions of the invention include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol 10, and octoxynol 9, poloxamers (polyoxyethylene and polyoxypropylene block copolymers), polyoxyethylene fatty acid glycerides and oils, for example polyoxyethylene (8) caprylic/capric mono- and diglycerides (e.g., Labrasol™ of Gattefosse), polyoxyethylene (35) castor oil and polyoxyethylene (40) hydrogenated castor oil; polyoxyethylene alkyl ethers, for example polyoxyethylene (20) cetostearyl ether, polyoxyethylene fatty acid esters, for example polyoxyethylene (40) stearate, polyoxyethylene sorbitan esters, for example polysorbate 20 and polysorbate 80 (e.g., Tween™ 80 of ICI), propylene glycol fatty acid esters, for example propylene glycol laurate (e.g., Lauroglycol™ of Gattefossé), sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof. Such wetting agents, if present, constitute in total about 0.25% to about 15%, preferably about 0.4% to about 10%, and more preferably about 0.5% to about 5%, of the total weight of the composition. Wetting agents that are anionic surfactants are preferred. Sodium lauryl sulfate is a particularly preferred wetting agent. Sodium lauryl sulfate, if present, constitutes about 0.25% to about 7%, more preferably about 0.4% to about 4%, and still more preferably about 0.5% to about 2%, of the total weight of the composition.

Compositions of the invention optionally comprise one or more pharmaceutically acceptable lubricants (including anti-adherents and/or glidants) as excipients. Suitable lubricants include, either individually or in combination, glyceryl behenate (e.g., Compritol™ 888); stearic acid and salts thereof, including magnesium, calcium and zinc stearates; hydrogenated vegetable oils (e.g., Sterotex™); colloidal silica; talc; waxes; sodium benzoate; sodium fumarate; PEG (e.g., Carbowax™ 4000 and Carbowax™ 6000); sodium oleate; sodium lauryl sulfate; and magnesium lauryl sulfate. Such lubricants, if present, constitute in total about 0.1% to about 10%, preferably about 0.2% to about 8%, and more preferably about 0.25% to about 5%, of the total weight of the composition. Magnesium stearate is a preferred lubricant used, for example, to reduce friction between the equipment and granulated mixture during compression of tablet formulations.

Suitable anti-adherents include talc, cornstarch, sodium lauryl sulfate and metallic stearates. Talc is a preferred anti-adherent or glidant used, for example, to reduce formulation sticking to equipment surfaces and also to reduce static in the blend. Talc, if present, constitutes about 0.1% to about 10%, more preferably about 0.25% to about 5%, and still more preferably about 0.5% to about 2%, of the total weight of the composition.

Glidants can be used to promote powder flow of a solid formulation. Suitable glidants include colloidal silicon dioxide, starch, talc, tribasic calcium phosphate, powdered cellulose and magnesium trisilicate. Colloidal silicon dioxide is particularly preferred. Other excipients such as colorants, flavors and sweeteners are known in the pharmaceutical art and can be used in compositions of the present invention. Tablets can be coated, for example with an enteric coating, or uncoated. Compositions of the invention can further comprise, for example, buffering agents. Optionally, one or more effervescent agents can be used as disintegrants and/or to enhance organoleptic properties of compositions of the invention. When present in compositions of the invention to promote dosage form disintegration, one or more effervescent agents are preferably present in a total amount of about 30% to about 75%, and preferably about 45% to about 70%, for example about 60%, by weight of the composition.

According to a particularly preferred embodiment of the invention, an effervescent agent, present in a solid dosage form in an amount less than that effective to promote disintegration of the dosage form, provides improved dispersion of the AMG 706 in an aqueous medium. When present in a pharmaceutical composition of the invention to promote intragastrointestinal dispersion but not to enhance disintegration, an effervescent agent is preferably present in an amount of about 1% to about 20%, more preferably about 2.5% to about 15%, and still more preferably about 5% to about 10%, by weight of the composition. An "effervescent agent" herein is an agent comprising one or more compounds which, acting together or individually, evolve a gas on contact with water. The gas evolved is generally carbon dioxide. Preferred effervescent agents comprise an acid and a base that react in the presence of water to generate carbon dioxide gas. Preferably, the base comprises an alkali metal or alkaline earth metal carbonate or bicarbonate and the acid comprises an aliphatic carboxylic acid. Non-limiting examples of suitable bases as components of effervescent agents useful in the invention include carbonate salts (e.g., calcium carbonate), bicarbonate salts (e.g., sodium bicarbonate), sesquicarbonate salts, and mixtures thereof. Calcium carbonate is a preferred base. Non-limiting examples of suitable acids as components of effervescent agents useful in the invention include citric acid, tartaric acid, malic acid, fumaric acid, adipic acid, succinic acid, acid anhydrides of such acids, acid salts of such acids, and mixtures thereof. Citric acid is a preferred acid. In a preferred embodiment of the invention, where the effervescent agent comprises an acid and a base, the weight ratio of the acid to the base is about 1:100 to about 100:1, more preferably about 1:50 to about 50:1, and still more preferably about 1:10 to about 10:1. In a further preferred embodiment of the invention, where the effervescent agent comprises an acid and a base, the ratio of the acid to the base is approximately stoichiometric.

Solid dosage forms of the invention can be prepared by any suitable process, not limited to processes described herein. An illustrative process comprises (a) a step of blending amorphous AMG 706, AMG 706 drug substance, or an AMG 706-crystallization inhibitor composite of the invention with one or more excipients to form a blend, and (b) a step of tableting or encapsulating the blend to form tablets or capsules respectively. In a preferred process, solid dosage forms are prepared by a process comprising (a) a step of blending amorphous AMG 706, AMG 706 drug substance, or an AMG 706-crystallization inhibitor composite of the invention with one or more excipients to form a blend, (b) a step of granulating the blend to form a granulate, and (c) a step of tableting or encapsulating the blend to form tablets or capsules respectively. Step (b) can be accomplished by any dry or wet granulation technique known in the art, but is preferably a wet granulation step followed by a step of drying the resulting granulate prior to tableting or encapsulating. One or more diluents, one or more disintegrants and one or more binding agents are preferably added, for example in the blending step, a wetting agent can optionally be added, for example in the granulating step, and one or more disintegrants are preferably added after granulating but before tableting or encapsulating. A lubricant is preferably added before tableting. Blending and granulating can be performed independently under low or high shear. A process is preferably selected that forms a granulate that is uniform in drug content, that readily disintegrates, that flows with sufficient ease so that weight variation can be reliably controlled during capsule filling or tableting, and that is dense enough in bulk so that a batch can be processed in the selected equipment and individual doses fit into the specified capsules or tablet dies.

In an alternative embodiment, solid dosage forms are prepared by a process that includes a spray drying step, wherein the amorphous AMG 706, AMG 706 drug substance or AMG 706-crystallization inhibitor composite is suspended with one or more excipients in one or more sprayable liquids, preferably a non-aqueous sprayable liquid, and then is rapidly spray dried over a current of warm air. This spray drying process for preparing a pharmaceutical composition can be performed in addition to any spray drying step used in preparation of an AMG 706-crystallization inhibitor composite as described hereinabove, but formation of the AMG 706-crystallization inhibitor composite is preferably combined with a spray drying step for preparation of the pharmaceutical composition. A granulate or spray dried powder resulting from any of the above illustrative processes can be compressed or molded to prepare tablets or encapsulated to prepare capsules. Conventional tableting and encapsulation techniques known in the art can be employed. Where coated tablets are desired, conventional coating techniques are suitable.

Any tablet hardness convenient with respect to handling, manufacture, storage and ingestion can be employed. The material to be tableted, however, should not be compressed to such a degree that there is subsequent difficulty in achieving hydration when exposed to gastric fluid.

AMG 706 Dosage

AMG 706 dosage forms of the invention preferably comprise AMG 706 in a daily dosage amount of about 10 mg to about 1000 mg, more preferably about 25 mg to about 400 mg, and most preferably about 50 mg to about 200 mg. Compositions of the invention comprise one or more orally deliverable dose units. Each dose unit comprises AMG 706 in a therapeutically effective amount that is preferably about 10 mg to about 1000 mg. The term "dose unit" herein means a portion of a pharmaceutical composition that contains an amount of a therapeutic or prophylactic agent, in the present case AMG 706, suitable for a single oral administration to provide a therapeutic effect. Typically one dose unit, or a small plurality (up to about 5) of dose units, in a single administration provides a dose comprising a sufficient amount of the agent to result in the desired effect. Administration of such doses can be repeated as required, typically at a dosage frequency of 1 to about 4 times per day. It will be understood that a therapeutically effective amount of AMG 706 for a subject is dependent inter alia on the body weight of the subject. A "subject" herein to which a therapeutic agent or composition thereof can be administered includes a human patient of either sex and of any age, and also includes any nonhuman animal, particularly a warm-blooded animal, more particularly a domestic or companion animal, illustratively a cat, dog or horse. When the subject is a child or a small animal (e.g., a dog), for example, an amount of AMG 706 relatively low in the preferred range of about 10 mg to about 1000 mg is likely to provide blood serum concentrations consistent with therapeutic effectiveness. Where the subject is an adult human or a large animal (e.g., a horse), achievement of such blood serum concentrations of AMG 706 are likely to require dose units containing a relatively greater amount of AMG 706. Typical dose units in a composition of the invention contain about 10, 20, 25, 37.5, 50, 75, 100, 125, 150, 175, 200, 250, 300, 350 or 400 mg of AMG 706. For an adult human, a therapeutically effective amount of AMG 706 per dose unit in a composition of the present invention is typically about 50 mg to about 400 mg. Especially preferred amounts of AMG 706 per dose unit are about 100 mg to about 200 mg, for example about 100 mg or about 200 mg. A dose unit containing a particular amount of AMG 706 can be selected to accommodate any desired frequency of administration used to achieve a desired daily dosage. The daily dosage and frequency of administration, and therefore the selection of appropriate dose unit, depends on a variety of factors, including the age, weight, sex and medical condition of the subject, and the nature and severity of the condition or disorder, and thus may vary widely. The term "oral administration" herein includes any form of delivery of a therapeutic agent or a composition thereof to a subject wherein the agent or composition is placed in the mouth of the subject, whether or not the agent or composition is immediately swallowed. Thus "oral administration" includes buccal and sublingual as well as esophageal administration. Absorption of the agent can occur in any part or parts of the gastrointestinal tract including the mouth, esophagus, stomach, duodenum, ileum and colon. The term "orally deliverable" herein means suitable for oral administration.

Utility of Compositions of the Invention

Such compositions are useful in treatment of angiogenesis-related disorders in a subject, for example to inhibit tumor angiogenesis. Such compositions are useful in treatment of neoplasia, including metastasis; ophthalmological conditions such as corneal graft rejection, ocular neovascularization, retinal neovascularization including neovascularization following injury or infection, diabetic retinopathy, macular degeneration, retrolental fibroplasia and neovascular glaucoma; ulcerative diseases such as gastric ulcer; pathological, but non-malignant, conditions such as hemangiomas, including infantile hemaginomas, angiofibroma of the nasopharynx and avascular necrosis of bone; and disorders of the female reproductive system such as endometriosis. Such compositions are useful in prevention and treatment of benign and malignant tumors and neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer, stomach cancer, colon cancer, liver cancer, bladder cancer, pancreas cancer, ovary cancer, cervical cancer, lung cancer, breast cancer, skin cancer such as squamous cell and basal cell cancers, prostate cancer, renal cell carcinoma, and other known cancers that effect epithelial cells throughout the body. Neoplasias for which compositions of the invention are contemplated to be particularly useful are gastrointestinal cancer, Barrett's esophagus, liver cancer, bladder cancer, pancreatic cancer, ovarian cancer, prostate cancer, cervical cancer, lung cancer, breast cancer and skin cancer. Such compositions can be used to treat subjects having adenomatous polyps, including those with familial adenomatous polyposis (FAP). Additionally, such compositions can be used to prevent polyps from forming in patients at risk of FAP. Besides being useful for human treatment, compositions of the invention are useful for veterinary treatment of companion animals, exotic animals, farm animals, and the like, particularly mammals. More particularly, compositions of the invention are useful for treatment of angiogenesis mediated disorders in horses, dogs and cats.

Method of Treatment

The present invention is further directed to a therapeutic method of treating a condition or disorder where treatment with an anti-angiogenic drug is indicated, the method comprising oral administration of a composition of the invention to a subject in need thereof. The dosage regimen to prevent, give relief from, or ameliorate the condition or disorder preferably corresponds to once-a-day or twice-a-day treatment, but can be modified in accordance with a variety of factors. These include the type, age, weight, sex, diet and medical condition of the subject and the nature and severity of the disorder. Thus, the dosage regimen actually employed can vary widely and can therefore deviate from the preferred dosage regimens set forth above.

Initial treatment can begin with a dose regimen as indicated above. Treatment is generally continued as necessary over a period of several weeks to several months or years until the condition or disorder has been controlled or eliminated. Subjects undergoing treatment with a composition of the invention can be routinely monitored by any of the methods well known in the art to determine effectiveness of therapy. Continuous analysis of data from such monitoring permits modification of the treatment regimen during therapy so that optimally effective doses are administered at any point in time, and so that the duration of treatment can be determined. In this way, the treatment regimen and dosing schedule can be rationally modified over the course of therapy so that the lowest amount of the composition exhibiting satisfactory effectiveness is administered, and so that administration is continued only for so long as is necessary to successfully treat the condition or disorder.

While the compounds of the invention can be administered as the sole active pharmaceutical agent, they can also be used in combination with one or more compounds of the invention or other agents. When administered as a combination, the therapeutic agents can be formulated as separate compositions that are administered at the same time or sequentially at different times, or the therapeutic agents can be given as a single composition. The phrase "co-therapy" (or "combination-therapy"), in defining use of a compound of the present invention and another pharmaceutical agent, is intended to embrace administration of each agent in a sequential manner in a regimen that will provide beneficial effects of the drug combination, and is intended as well to embrace co-administration of these agents in a substantially simultaneous manner, such as in a single capsule having a fixed ratio of these active agents or in multiple, separate capsules for each agent. Specifically, the administration of compounds of the present invention may be in conjunction with additional therapies known to those skilled in the art in the prevention or treatment of neoplasia, such as with radiation therapy or with cytostatic or cytotoxic agents.

If formulated as a fixed dose, such combination products employ the compounds of this invention within the accepted dosage ranges. Compound of Formula I may also be administered sequentially with known anticancer or cytotoxic agents when a combination formulation is inappropriate. The invention is not limited in the sequence of administration; compounds of the invention may be administered either prior to, simultaneous with or after administration of the known anticancer or cytotoxic agent.

Currently, standard treatment of primary tumors consists of surgical excision followed by either radiation or IV administered chemotherapy. The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of neoplasia by combination drug chemotherapy. Such antineoplastic agents fall into several major categories, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention consists of antimetabolite-type/thymidilate synthase inhibitor antineoplastic agents. Suitable antimetabolite antineoplastic agents may be selected from but not limited to the group consisting of 5-FU-fibrinogen, acanthifolic acid, aminothiadiazole, brequinar sodium, carmofur, Ciba-Geigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5-fluorouracil, N-(2'-furanidyl)-5-fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC-788, thioguanine, tiazofurin, Erbamont TIF, trimetrexate, tyrosine kinase inhibitors, Taiho UFT and uricytin.

A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D-19-384, Sumimoto DACHP(Myr)$_2$, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G-6-M, Chinoin GYKI-17230, hepsul-fam, ifosfamide, iproplatin, lomustine, mafosfamide, mitolactol, Nippon Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN-201-H, Ajinomoto AN-3, Nippon Soda anisomycins, anthracycline, azino-mycin-A, bisucaberin, Bristol-Myers BL-6859, Bristol-Myers BMY-25067, Bristol-Myers BMY-25551, Bristol-Myers BMY-26605, Bristol-Myers BMY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko DC89-A1, Kyowa Hakko DC92-B, ditrisarubicin B, Shionogi DOB-41, doxorubicin, doxorubicin-fibrinogen, elsamicin-A, epirubicin, erbstatin, esorubicin, esperamicin-A1, esperamicin-Alb, Erbamont FCE-21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin, rhizoxin, rodorubicin, sibanomicin, siwenmycin, Sumitomo SM-5887, Snow Brand SN-706, Snow Brand SN-07, sorangicin-A, sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of α-carotene, α-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5, antineoplaston AS2-1, Henkel APD, aphidicolin glycinate, asparaginase, Avarol, baccharin, batracylin, benfluoron, benzotript, Ipsen-Beaufour BIM-23015, bisantrene, Bristol-Myers BMY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, Warner-Lambert CI-937, Warner-Lambert CI-941, Warner-Lambert CI-958, clanfenur, claviridenone, ICN compound 1259, ICN compound 4711, Contracan, Yakult Honsha CPT-11, crisnatol, curaderm, cytochalasin B, cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704, gallium nitrate, genkwadaphnin, Chugai GLA-43, Glaxo GR-63178, grifolan NMF-5N, hexadecylphosphocholine, Green Cross HO-221, homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU-23-112, Lilly LY-186641, NCI (US) MAP, marycin, Merrel Dow MDL-27048, Medco MEDR-340, merbarone, merocyanlne derivatives, methylanilinoacridine, Molecular Genetics MGI-136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP-49532, Rhone-Poulenc RP-56976, SmithKline SK&F-104864, Sumitomo SM-108, Kuraray SMANCS, SeaPharm SP-10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT-82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM-534.

Alternatively, the present compounds may also be used in co-therapies with other anti-neoplastic agents, such as acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab, eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-N1, interferon alfa-n3, interferon alfacon-1, interferon alpha, natural, interferon beta, interferon beta-1a, interferon beta-1b, interferon gamma, natural interferon gamma-1a, interferon gamma-1b, interleukin-1 beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofuran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinide, filgrastim SD01 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin-2, iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM-1-iodine 131 MAb (Techniclone), polymorphic epithelial mucin-yttrium 90 MAb (Antisoma), marimastat, menogaril, mitumomab, motexafin gadolinium, MX 6 (Galderma), nelarabine, nolatrexed, P 30 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Other compounds described in the following patents and patent applications can be used in combination therapy: U.S. Pat. No. 6,258,812, US 2003/0105091, WO 01/37820, U.S. Pat. No. 6,235,764, WO 01/32651, U.S. Pat. No. 6,630,500, U.S. Pat. No. 6,515,004, U.S. Pat. No. 6,713,485, U.S. Pat. No. 5,521,184, U.S. Pat. No. 5,770,599, U.S. Pat. No. 5,747,498, WO 02/68406, WO 02/66470, WO 02/55501, WO 04/05279, WO 04/07481, WO 04/07458, WO 04/09784, WO 02/59110, WO 99/45009, WO 00/59509, WO 99/61422, U.S. Pat. No. 5,990,141, WO 00/12089 and WO 00/02871.

In some embodiments, the combination comprises a composition of the present invention in combination with at least one anti-angiogenic agent. Agents are inclusive of, but not limited to, in vitro synthetically prepared chemical compositions, antibodies, antigen binding regions, radionuclides, and combinations and conjugates thereof. An agent can be an agonist, antagonist, allosteric modulator, toxin or, more generally, may act to inhibit or stimulate its target (e.g., receptor or enzyme activation or inhibition), and thereby promote cell death or arrest cell growth.

Exemplary anti-tumor agents include HERCEPTIN™ (trastuzumab), which may be used to treat breast cancer and other forms of cancer, and RITUXAN™ (rituximab), ZEVALIN™ (ibritumomab tiuxetan), and LYMPHOCIDE™ (epratuzumab), which may be used to treat non-Hodgkin's lymphoma and other forms of cancer, GLEEVAC™ which may be used to treat chronic myeloid leukemia and gastrointestinal stromal tumors, and BEXXAR™ (iodine 131 tositumomab) which may be used for treatment of non-Hodgkins's lymphoma.

Exemplary anti-angiogenic agents include ERBITUX™ (IMC-C225), KDR (kinase domain receptor) inhibitory agents (e.g., antibodies and antigen binding regions that specifically bind to the kinase domain receptor), anti-VEGF agents (e.g., antibodies or antigen binding regions that specifically bind VEGF, or soluble VEGF receptors or a ligand binding region thereof) such as AVASTIN™ or VEGF-TRAP™, and anti-VEGF receptor agents (e.g., antibodies or antigen binding regions that specifically bind thereto), EGFR inhibitory agents (e.g., antibodies or antigen binding regions that specifically bind thereto) such as VECTIBIX™ (panitumumab), NEXAVAR™ (sorafenib), SUTENT™ (sunitinib), IRESSA™ (gefitinib), TARCEVA™ (erlotinib), anti-Ang1 and anti-Ang2 agents (e.g., antibodies or antigen binding regions specifically binding thereto or to their receptors, e.g., Tie2/Tek), and anti-Tie2 kinase inhibitory agents (e.g., antibodies or antigen binding regions that specifically bind thereto). The pharmaceutical compositions of the present invention can also include one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

Other anti-angiogenic agents include Campath, IL-8, B-FGF, Tek antagonists (Ceretti et al., U.S. Publication No. 2003/0162712; U.S. Pat. No. 6,413,932), anti-TWEAK agents (e.g., specifically binding antibodies or antigen binding regions, or soluble TWEAK receptor antagonists; see, Wiley, U.S. Pat. No. 6,727,225), ADAM distintegrin domain to antagonize the binding of integrin to its ligands (Fanslow et al., U.S. Publication No. 2002/0042368), specifically binding anti-eph receptor and/or anti-ephrin antibodies or antigen binding regions (U.S. Pat. Nos. 5,981,245; 5,728,813; 5,969,110; 6,596,852; 6,232,447; 6,057,124 and patent family members thereof), and anti-PDGF-BB antagonists (e.g., specifically binding antibodies or antigen binding regions) as well as antibodies or antigen binding regions specifically binding to PDGF-BB ligands, and PDGFR kinase inhibitory agents (e.g., antibodies or antigen binding regions that specifically bind thereto).

Additional anti-angiogenic/anti-tumor agents include: SD-7784 (Pfizer, USA); cilengitide. (Merck KGaA, Germany, EPO 770622); pegaptanib octasodium, (Gilead Sciences, USA); Alphastatin, (BioActa, UK); M-PGA, (Celgene, USA, U.S. Pat. No. 5,712,291); ilomastat, (Arriva, USA, U.S. Pat. No. 5,892,112); emaxanib, (Pfizer, USA, U.S. Pat. No. 5,792,783); vatalanib, (Novartis, Switzerland); 2-methoxyestradiol, (EntreMed, USA); TLC ELL-12, (Elan, Ireland); anecortave acetate, (Alcon, USA); alpha-D148 Mab, (Amgen, USA); CEP-7055, (Cephalon, USA); anti-Vn Mab, (Crucell, Netherlands) DAC; antiangiogenic, (ConjuChem, Canada); Angiocidin, (InKine Pharmaceutical, USA); KM-2550, (Kyowa Hakko, Japan); SU-0879, (Pfizer, USA); CGP-79787, (Novartis, Switzerland, E P 970070); ARGENT technology, (Ariad, USA); YIGSR-Stealth, (Johnson & Johnson, USA); fibrinogen-E fragment, (BioActa, UK); angiogenesis inhibitor, (Trigen, UK); TBC-1635, (Encysive Pharmaceuticals, USA); SC-236, (Pfizer, USA); ABT-567, (Abbott, USA); Metastatin, (EntreMed, USA); angiogenesis inhibitor, (Tripep, Sweden); maspin, (Sosei, Japan); 2-methoxyestradiol, (Oncology Sciences Corporation, USA); ER-68203-00, (IVAX, USA); Benefin, (Lane Labs, USA); Tz-93, (Tsumura, Japan); TAN-1120, (Takeda, Japan); FR-111142, (Fujisawa, Japan, JP 02233610); platelet factor 4, (RepliGen, USA, EP 407122); vascular endothelial growth factor antagonist, (Borean, Denmark); cancer therapy, (University of South Carolina, USA); bevacizumab (pINN), (Genentech, USA); angiogenesis inhibitors, (SUGEN, USA); XL 784, (Exelixis, USA); XL 647, (Exelixis, USA); MAb, alpha5beta3 integrin, second generation, (Applied Molecular Evolution, USA and MedImmune, USA); gene therapy, retinopathy, (Oxford BioMedica, UK); enzastaurin hydrochloride (USAN), (Lilly, USA); CEP 7055, (Cephalon, USA and Sanofi-Synthelabo, France); BC 1, (Genoa Institute of Cancer Research, Italy); angiogenesis inhibitor, (Alchemia, Australia); VEGF antagonist, (Regeneron, USA); rBPI 21 and BPI-derived antiangiogenic, (XOMA, USA); PI 88, (Progen, Australia); cilengitide (pINN), (Merck KGaA, German; Munich Technical University, Germany, Scripps Clinic and Research Foundation, USA); cetuximab (INN), (Aventis, France); AVE 8062, (Ajinomoto, Japan); AS1404, (Cancer Research Laboratory, New Zealand); SG 292, (Telios, USA); Endostatin, (Boston Childrens Hospital, USA); ATN 161, (Attenuon, USA); ANGIOSTATIN, (Boston Childrens Hospital, USA); 2-methoxyestradiol, (Boston Childrens Hospital, USA); ZD 6474, (AstraZeneca, UK); ZD 6126, (Angiogene Pharmaceuticals, UK); PPI 2458, (Praecis, USA); AZD 9935, (AstraZeneca, UK); AZD 2171, (AstraZeneca, UK); vatalanib (pINN), (Novartis, Switzerland and Schering A G, Germany); tissue factor pathway inhibitors, (EntreMed, USA); pegaptanib (Pinn), (Gilead Sciences, USA); xanthorrhizol, (Yonsei University, South Korea); vaccine, gene-based, VEGF-2, (Scripps Clinic and Research Foundation, USA); SPV5.2, (Supratek, Canada); SDX 103, (University of California at San Diego, USA); PX 478, (ProlX, USA); METASTATIN, (EntreMed, USA); troponin I, (Harvard University, USA); SU 6668, (SUGEN, USA); OXI 4503, (OXiGENE, USA); o-guanidines, (Dimensional Pharmaceuticals, USA); motuporamine C, (British Columbia University, Canada); CDP 791, (Celltech Group, UK); atiprimod (pINN), (GlaxoSmithKline, UK); E 7820, (Eisai, Japan); CYC 381, (Harvard University, USA); AE 941, (Aeterna, Canada); vaccine, angiogenesis, (EntreMed, USA); urokinase plasminogen activator inhibitor, (Dendreon, USA); oglufanide (pINN), (Melmotte, USA); HIF-1alfa inhibitors, (Xenova, UK); CEP 5214, (Cephalon, USA); BAY RES 2622, (Bayer, Germany); Angiocidin, (InKine, USA); A6, (Angstrom, USA); KR 31372, (Korea Research Institute of Chemical Technology, South Korea); GW 2286, (GlaxoSmithKline, UK); EHT 0101, (ExonHit, France); CP 868596, (Pfizer, USA); CP 564959, (OSI, USA); CP 547632, (Pfizer, USA); 786034, (GlaxoSmithKline, UK); KRN 633, (Kirin Brewery, Japan); drug delivery system, intraocular, 2-methoxyestradiol, (EntreMed, USA); anginex, (Maastricht University, Netherlands, and Minnesota University, USA); ABT 510, (Abbott, USA); AAL 993, (Novartis, Switzerland); VEGI, (ProteomTech, USA); tumor necrosis factor-alpha inhibitors, (National Institute on Aging, USA); SU 11248, (Pfizer, USA and SUGEN USA); ABT 518, (Abbott, USA); YH16, (Yantai Rongchang, China); S-3APG, (Boston Childrens Hospital, USA and EntreMed, USA); MAb, KDR, (ImClone Systems, USA); MAb, alpha5 beta1, (Protein Design, USA); KDR kinase inhibitor, (Celltech Group, UK, and Johnson & Johnson, USA); GFB 116, (South Florida University, USA and Yale University, USA); CS 706, (Sankyo, Japan); combretastatin A4 prodrug, (Arizona State University, USA); chondroitinase AC, (IBEX, Canada); BAY RES 2690, (Bayer, Germany); AGM 1470, (Harvard University, USA, Takeda, Japan, and TAP, USA); AG 13925, (Agouron, USA); Tetrathiomolybdate, (University of Michigan, USA); GCS100, (Wayne State University, USA) CV 247, (Ivy Medical, UK); CKD 732, (Chong Kun Dang, South Korea); MAb, vascular endothelium growth factor, (Xenova, UK); irsogladine (INN), (Nippon Shinyaku, Japan); RG 13577, (Aventis, France); WX 360, (Wilex, Germany); squalamine (pINN), (Genaera, USA); RPI 4610, (Sirna, USA); cancer therapy, (Marinova, Australia); heparanase inhibitors, (InSight, Israel); KL 3106, (Kolon, South Korea); Honokiol, (Emory University, USA); ZK CDK, (Schering A G, Germany); ZK Angio, (Schering A G, Germany); ZK 229561, (Novartis, Switzerland, and Schering A G, Germany); XMP 300, (XOMA, USA); VGA 1102, (Taisho, Japan); VEGF receptor modulators, (Pharmacopeia, USA); VE-cadherin-2 antagonists, (ImClone Systems, USA); Vasostatin, (National Institutes of Health, USA); vaccine, Flk-1, (ImClone Systems, USA); TZ 93, (Tsumura, Japan); TumStatin, (Beth Israel Hospital, USA); truncated soluble FLT 1 (vascular endothelial growth factor receptor 1), (Merck & Co, USA); Tie-2 ligands, (Regeneron, USA); and, thrombospondin 1 inhibitor, (Allegheny Health, Education and Research Foundation, USA).

Alternatively, the present compounds may also be used in co-therapies with other anti-neoplastic agents, such as VEGF antagonists, other kinase inhibitors including p38 inhibitors, KDR inhibitors, EGF inhibitors and CDK inhibitors, TNF inhibitors, metallomatrix proteases inhibitors (MMP), COX-2 inhibitors including celecoxib, NSAID's, or $\alpha_v\beta_3$ inhibitors.

The compound to be administered in combination with AMG 706 can be formulated separately from the AMG 706 or co-formulated with the AMG 706 in a composition of the invention. Where AMG 706 is co-formulated with a second drug, the second drug can be formulated in immediate-release, rapid-onset, sustained-release or dual-release form.

Processes for preparing AMG 706

Formula 1 are set forth in WO02/066470 and US 2003/0225106, incorporated herein by reference.

EXAMPLES

The following examples illustrate aspects of the present invention but are not to be construed as limitations.

Example 1

Amorphous AMG 706 drug substance was prepared by the following spray drying process. About 1.5 grams of crystalline AMG 706 was weighed and transferred to a 250 mL Erlenmeyer flask and dissolved in 150 mL deionized water. The solution was spray dried under the following conditions:

| | |
|---|---|
| Atomization pressure: | 50 psi |
| Nitrogen drying flow rate: | 650 SLPM |
| Inlet temperature: | 165° C. |
| Outlet temperature: | 108° C. |
| Solution flow rate: | 1 mL/min |

DSC, MDSC and XRPD analysis was performed on the material.

Example 2

Amorphous AMG 706 drug substance was prepared by the following lyophilization process. About 3.5 grams of crystalline AMG 706 was weighed and transferred to a large petri dish and dissolved by addition of 175 mL of deionized water. The solution was frozen using an FTS freeze dryer by cooling to −40° C. at a rate of 2.5° C./min and held for an hour and then adjusted the vacuum to 15 mT. The freezing cycle consisted of a 2.5° C./min ramp to −40° C. and a hold of 60 min. The vacuum pump was turned on when the condenser temperature reached −40° C. The method chamber vacuum was set to 250 mT to start the drying cycle. The drying cycle ramped at 2.5° C./min to a shelf temperature of −40° C. and held for 1240 min with vacuum set to 15 mT. The temperature increased to 20° C. at 1240 min and was held for another 1000 min at 15 mT. The sample was removed after 24 hours of drying.

Example 3

The X-ray powder diffraction (XRPD) data were obtained from either a Shimadzu x-ray diffractometer (LabX XRD-6000, Shimadzu) or a Philips x-ray diffractometer (X'Pert Pro, PANalytical). The radiation was Cu Kα (40 kV, 40 mA) from XRD-6000 and the data were collected by a proportional detector at room temperature from 2.5 to 40° C. with step size of 0.02 degree; speed at 1.0 deg/min; and count time of 12 sec/step. The radiation was Cu Kα (45 kV, 40 mA) from X' pert Pro. Under continuous scan mode, the data were collected by X'Celerator dector at room temperature from 3 to 40° C. with step size of 0.0084 degree and speed at 0.0005.

Figure 1:
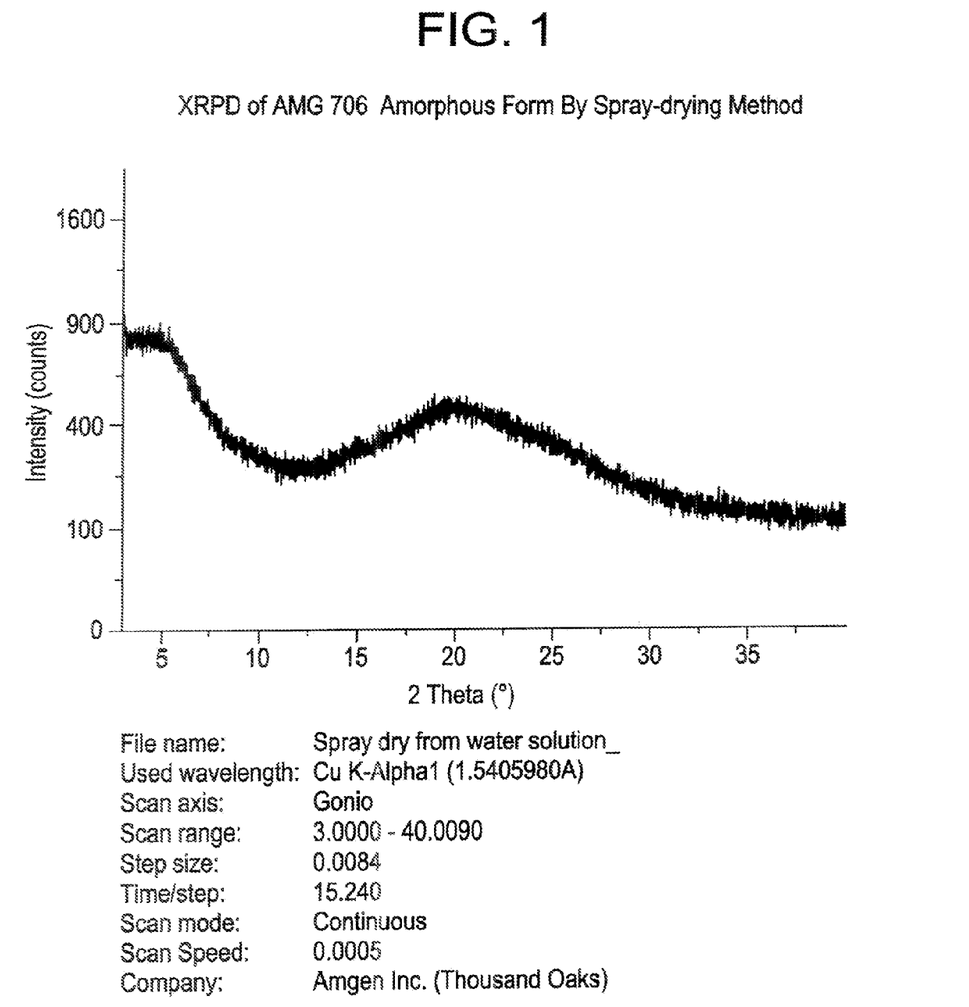
FIG. 1 shows a powder X-ray diffraction (XRPD) profile of AMG 706 drug substance prepared by a spray drying method of Example 1.
Figure 3:
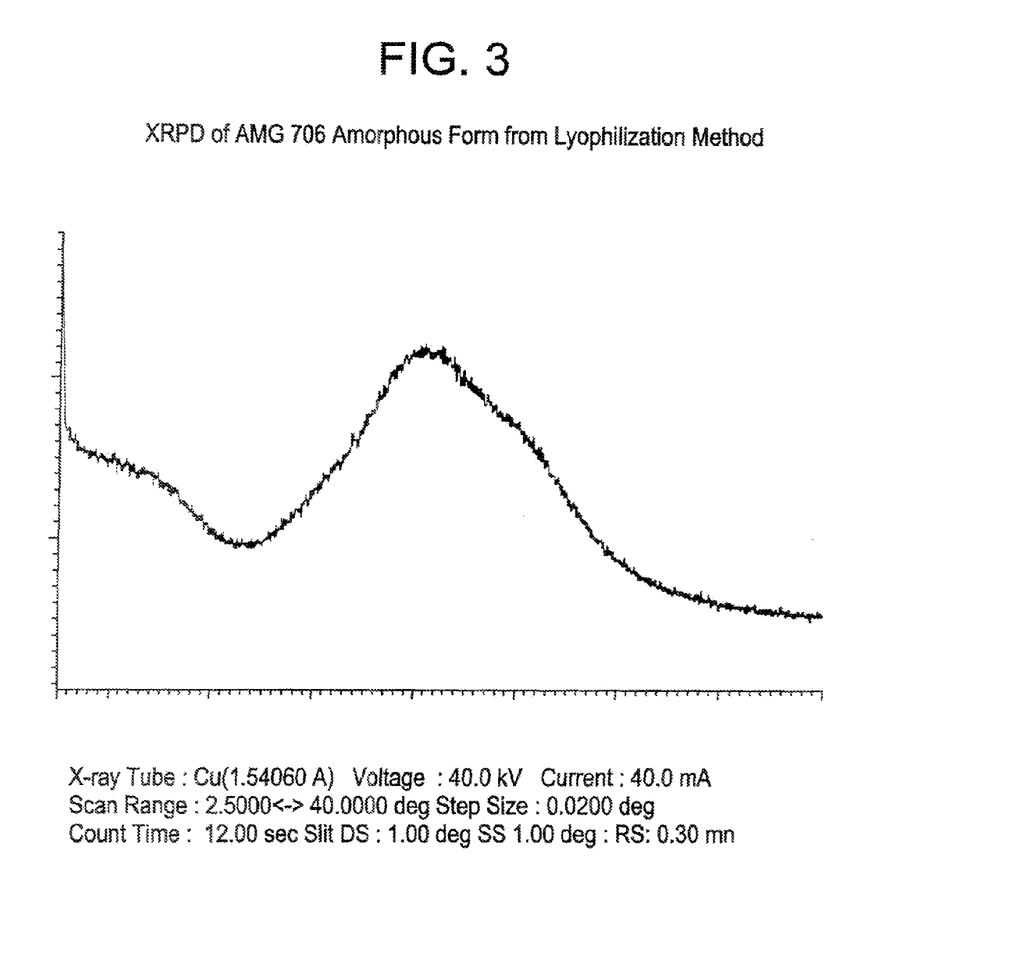
FIG. 3 shows a powder X-ray diffraction (XRPD) profile of AMG 706 drug substance prepared by the lyophilization method described in Example 2.

The results of the XRPD analyses of the amorphous materials are shown as bands in FIGS. 1 and 3. The appearance of compressed peaks is indicative of amorphous material whereas a lack of larger, spiked peaks on a band indicates a lack of crystallinity.

FIG. 1 shows that AMG 706 produced by spray drying produces amorphous material with no crystalline material observable by XRPD.

FIG. 3 shows that when AMG 706 produced by lyophilization produces amorphous material with no crystalline material observable by XRPD.

Figure 5:
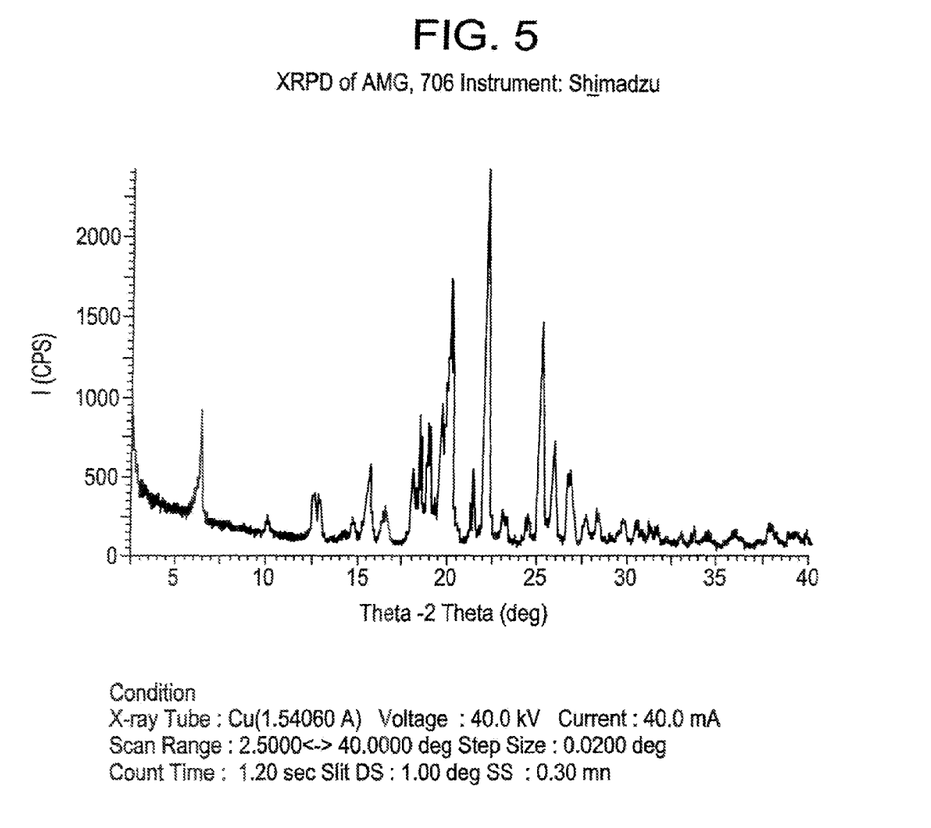
FIG. 5 shows a powder X-ray diffraction (XRPD) profile of crystalline AMG 706 drug substance.

FIG. 5 shows the peaks associated with crystalline AMG 706 observable by XRPD.

Example 4

Differential Scanning Calorimetry (DSC) and Modulated Differential Scanning Calorimetry (MDSC)

The thermal property of AMG 706-21 amorphous material was characterized with differential scanning calorimetry or modulated differential scanning calorimetry (Q100, TA Instrument). For modulated differential scanning calorimetry, approximately 1 mg samples were weighed into a non-hermetically crimpled aluminum pans and heated at 2° C./min with modulation amplitude off 1.2° C. every 60 seconds. For differential scanning calorimetry, samples were weighed into a nonhermetically crippled aluminum pans and heated at 10° C./min.

Figure 2:
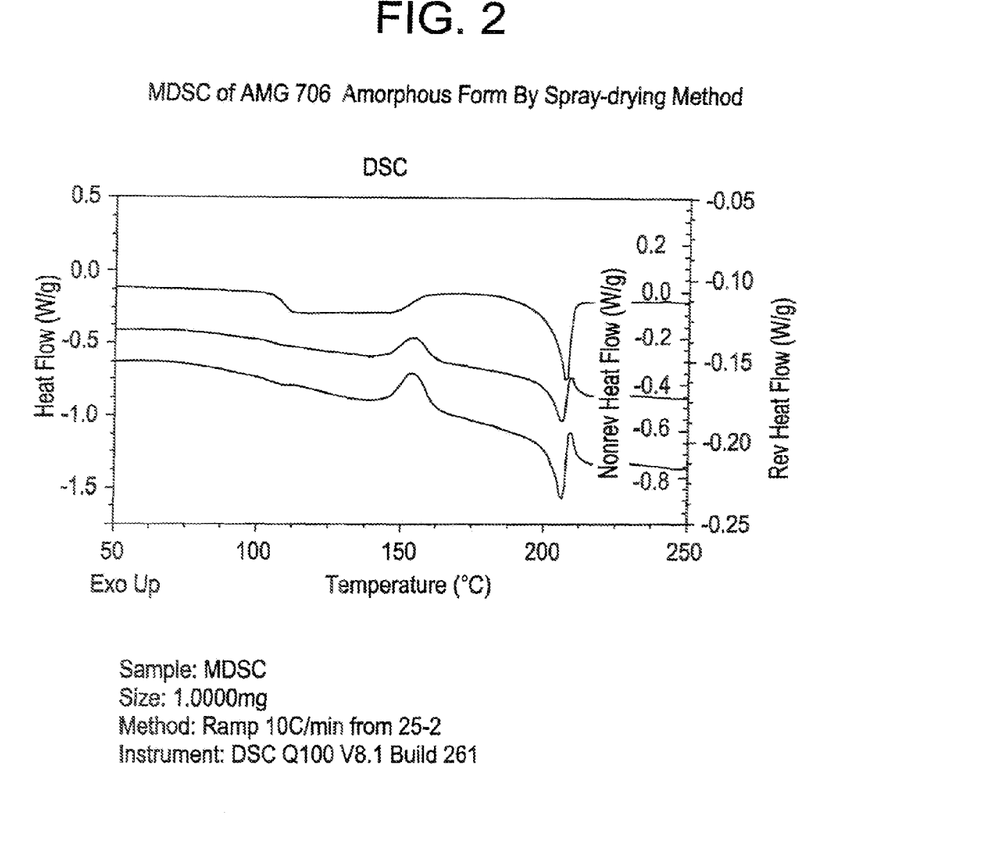
FIG. 2 shows a differential scanning calorimetry (DSC) thermogram of AMG 706 drug substance prepared by a spray drying method of Example 1.
Figure 4:
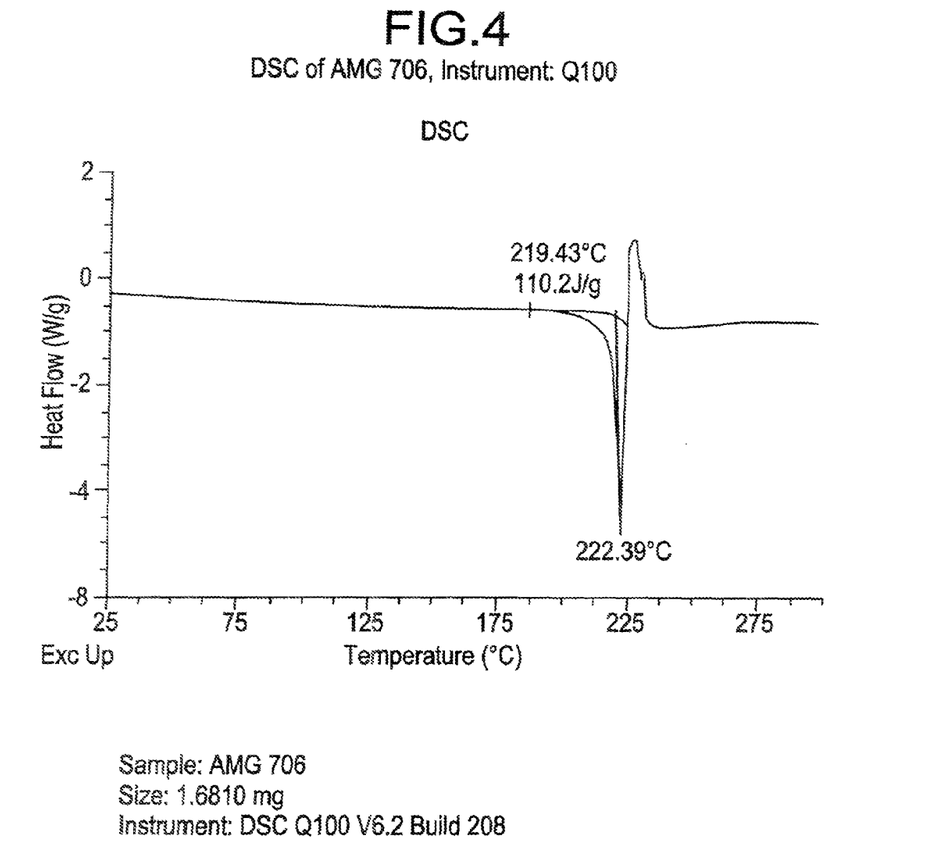
FIG. 4 shows a differential scanning calorimetry (DSC) thermogram of crystalline AMG 706 drug substance.

FIG. 2 shows DSC thermogram for the spray dried powder of Example 1. A first significant thermal event was observed at about 110° C., representing a glass transition temperature indicative of amorphous AMG 706. An exothermic peak observed at 150-160° C. was consistent with a crystallization event and represents conversion of amorphous AMG 706 to a crystalline state. As was shown by the presence of an endothermic peak, the resulting crystalline AMG 706 melted and decomposed at about 215° C. FIG. 4 shows DSC thermogram for the standard crystalline AMG 706.

Although this invention has been described with respect to specific embodiments, the details of these embodiments are not to be construed as limitations.

What is claimed is:

1. A process for preparing amorphous form of N-(2,3-dihydro-3,3-dimethyl-1H-indol-6-yl)-2-[(4-pyridinylmethyl)amino]-3-pyridinecarboxamide, diphosphate salt, wherein the amorphous form has a DSC thermogram that lacks a melting point above about 200° C., comprising the steps of:
    preparing a solution of N-(2,3-dihydro-3,3-dimethyl-1H-indol-6-yl)-2-[(4-pyridinylmethyl)amino]-3-pyridinecarboxamide, diphosphate salt and water; and
    removing the water.

2. The process of claim 1 wherein removing the water is accomplished by spray drying.

3. The process of claim 1 wherein removing the water is accomplished by lyophilization.

* * * * *